(12) United States Patent
Bornhoft

(10) Patent No.: US 9,789,289 B2
(45) Date of Patent: Oct. 17, 2017

(54) SYSTEMS AND METHODS FOR PROVIDING AN INTEGRATED PACKAGE AND GRIP FOR CATHETER

(71) Applicant: Becton, Dickinson and Company, Franklin Lakes, NJ (US)

(72) Inventor: Stephen T. Bornhoft, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 575 days.

(21) Appl. No.: 14/260,049

(22) Filed: Apr. 23, 2014

(65) Prior Publication Data

US 2015/0306351 A1    Oct. 29, 2015

(51) Int. Cl.
  *A61M 25/06* (2006.01)
  *A61M 25/00* (2006.01)

(52) U.S. Cl.
  CPC ........ *A61M 25/065* (2013.01); *A61M 25/002* (2013.01); *A61M 25/0606* (2013.01)

(58) Field of Classification Search
  CPC .......... A61M 5/31586; A61M 5/31581; A61M 2025/0175; A61M 5/3243; A61M 5/3202; A61M 5/1626; A61M 5/50; A61B 50/3001
  See application file for complete search history.

(56) References Cited

U.S. PATENT DOCUMENTS

| 5,133,454 | A | * | 7/1992 | Hammer | ............... A61M 5/002 |
|||||| 206/364 |
| 5,176,650 | A | * | 1/1993 | Haining | ............ A61M 25/0631 |
|||||| 604/164.08 |
| 6,186,325 | B1 | | 2/2001 | Schmidt et al. | |
| 2014/0074031 | A1 | | 3/2014 | Bornhoft | |
| 2014/0323857 | A1 | * | 10/2014 | Mourad | ................... A61B 8/12 |
|||||| 600/424 |

FOREIGN PATENT DOCUMENTS

WO    2008/064327 A2    5/2008

* cited by examiner

*Primary Examiner* — Nathan R Price
*Assistant Examiner* — Melissa A Snyder
(74) *Attorney, Agent, or Firm* — Jeanne Lukasavage; Craig Metclaf; Kirton McConkie

(57) ABSTRACT

An integrated individual package and an introducer needle or wire for placing a catheter in a patient's vasculature, wherein the package doubles as a grip for placing the catheter. Prior to activation, the catheter is coaxially and slidably disposed over the introducer needle and the catheter and introducer needle assemblies are contained within the integrated package grip. The device is activated as the catheter and introducer needle assemblies are simultaneously transitioned from a closed position to an open position wherein the catheter and introducer needle assemblies are oriented for insertion into a patient's vasculature. Following placement of the catheter in a patient's vasculature, the device is deactivated as the introducer needle is withdrawn and transitioned from the open position to resume the closed position. The package grip comprises a sharps shuttle to protect a clinician from needle stick injuries.

13 Claims, 17 Drawing Sheets

SYSTEMS AND METHODS FOR PROVIDING AN INTEGRATED PACKAGE AND GRIP FOR CATHETER

FIELD OF THE INVENTION

The present invention relates to systems and methods for providing an integrated package and gripping device for a catheter. The device of the present invention is used as a package to safely store and transport a sterile catheter prior to use and then, in conjunction with an introducer needle or guide wire, as a handle or grip to place or insert the catheter into a patient's vasculature. The package then doubles as a sharps shuttle for the safe disposal of the introducer needle or guide wire.

BACKGROUND OF THE INVENTION

Catheters, such as standard peripheral I.V. catheters and the like, are commonly used in the medical field and by clinicians to introduce pharmaceuticals and other treatments or medications into a patient's blood stream. Catheters are also useful for permitting various patient fluids to be drained or collected. Accordingly, various technologies have been developed or otherwise evolved over time for placing catheters into a patient's vasculature. For example, common devices include introducer needles or guide wires to assist a clinician in inserting and placing a catheter into a patient's vasculature. In addition, a needle hub used in connection with such introducer needles or guide wires and is handled directly by the user according to common practice.

Typically, the individual package is a separate device from the catheter unit and needle assembly. A clinician must remove and discard the packaging associated with one or more devices in order to place the catheter into the patient's vasculature. In an emergency situation, or in a situation where time is critical, this step of removing the device from its package adds time. Additionally, once the user removes the device from its packaging it may fall out of their grasp causing contamination, as well as damage and/or loss of the device. This loose packaging also causes added waste to a medical environment already cluttered with waste. Furthermore, once the catheter placement device is ready and following use of the same, the clinician is at risk of needle stick injuries both before and after the introducer needle is contaminated from use. As such, the clinician must take caution to prevent such injuries. Likewise, once the catheter placement device is ready, the sterility of the catheter is subject to compromise if not used immediately and the clinician must cautiously guard against the same.

Following use of the catheter placement device, the introducer needle and needle hub must be properly discarded for disposal using and appropriate biohazard container. The individual package may simply be discarded in any waste disposal bin. If the introducer needle does not feature a sharps injury protection feature, on the other hand, the needle point continues to pose a risk of needle stick injuries and blood borne illnesses. As such, the introducer needle must be carefully disposed of in an appropriate sharps container. In an emergency situation, the clinician must exercise particular caution to prevent needle stick injuries prior to the proper disposal of the introducer needle. Moreover, a separate sharps container is necessary.

In some instances, particularly in emergency situations, the catheter placement device is subject to inadvertently being gripped incorrectly such that the introducer needle and catheter are not oriented for proper placement by the clinician. In such circumstances, the clinician must take time and care to ensure that the catheter placement device is both properly gripped and properly oriented in order to correctly place the catheter in a patient's vasculature.

Thus, while techniques currently exist that are used for placing a catheter into a patient's vasculature, challenges still exist. Accordingly, it would be an improvement in the art to augment or even replace current techniques with other techniques.

BRIEF SUMMARY OF THE INVENTION

The present invention relates to systems and methods for providing an integrated package and gripping device for a catheter. The device of the present invention is used as a package to safely store and transport a sterile catheter prior to use and then, in conjunction with an introducer needle or guide wire, as a handle or grip to place or insert the catheter into a patient's vasculature. The package then doubles as a sharps shuttle for the safe disposal of the introducer needle or guide wire.

According to various embodiments, the integrated package and gripping device of the presentation invention generally includes a catheter assembly, an introducer needle assembly, and a package grip assembly. In some embodiments, the catheter is coaxially and slidably disposed over the introducer needle and the catheter and introducer needle assemblies are contained within the integrated package grip prior to activation of the device. The device is activated as the catheter and introducer needle assemblies are simultaneously transitioned from a closed position to an open position wherein the catheter and introducer needle assemblies are oriented for insertion into a patient's vasculature. In some embodiments, following placement of the catheter in a patient's vasculature, the device is deactivated as the introducer needle is withdrawn and transitioned from the open position to resume the closed position. In some embodiments, the package grip comprises a sharps shuttle to protect a clinician from needle stick injuries.

The package grip assembly, and associated components thereof, are shaped, sized and otherwise ergonomically configured to facilitate manual dexterity of the device. In some embodiments, the package grip assembly includes features or components to further enhance such manual dexterity. For example, in some embodiments, the package grip assembly includes wings formations or gripping protrusions having convex and/or concave surfaces adapted to compliment that natural curvature and shape of a user's fingers or grip. In other embodiments, the package grip assembly includes gripping formations, such as ridges or grooves, integrally formed or attached to the external surfaces of the package grip assembly. In still other embodiments, the package grip assembly is formed, or includes formations, such as an external ridge or flange, configured to encourage the user to grip the device in the proper way or orientation to facilitate placement of the catheter into a patient's vasculature.

In some embodiments, the device comprises a hinge coupling assembly between the package grip assembly and the catheter and introducer needle sub-assemblies. In such embodiments, the device is activated or otherwise transitioned from a closed position to an open position via the hinge coupling assembly. According to other embodiments, the device comprises a sliding guide track coupling between the package grip assembly and the catheter and introducer needle sub-assemblies. In such embodiments, the device is activated or otherwise transitioned from a closed position to an open position via the sliding guide track assembly.

In various embodiments, additional features, such as a temporarily affixed sealing label, a push tab, one or more springs, or a push-button mechanism, may also be used in connection with either the hinge coupling assembly or the sliding guide track assembly in order to activate the device. The device is deactivated by reversing the activating transition such that the device is returned from an open position to the closed position via the coupling assembly and/or additional components associated therewith. In this way, the introducer needle may be safely shuttled and disposed of following use. According to various embodiments, the device is configured so as to be temporarily biased or locked in either the open position or the closed position as desired prior to, during, or after use.

Following activation, the device is gripped in a proper orientation, which in some embodiments is encouraged by the shape, size, formation, or other features of the package grip assembly. When properly gripped, the device is used to place a catheter at a desired location suitable for establishing a fluid communication pathway with the patient's vasculature. This may be accomplished according to various techniques known to those of skill in the art. For example, following activation of the device, the clinician substantially longitudinally aligns the introducer needle and the catheter with a target blood vessel. The clinician then proceeds to insert the introducer needle and the catheter at a shallow angle into the patient's skin so that the sharp tip thereof enters the target blood vessel. According to some embodiments, after confirming placement of the introducer needle and the catheter in the target blood vessel, the clinician advances the catheter into position in the blood vessel. The clinician then withdraws the introducer needle from the catheter. The device is then deactivated such that the introducer needle is returned to the closed position and the package grip assembly acts as a sharps shuttle for the safe transportation and disposal of the used device.

In some embodiments, the device further includes an additional sharps injury protection feature such as a shroud or shield disposed about the introducer needle such that, upon complete removal of the introducer needle from the catheter, the needle shroud locks over the tip of the needle thus preventing unwanted proximal and distal movement of sharp tip once the tip has been fully withdrawn into the needle shield. Active or passive sharps injury protection features are contemplated.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict typical embodiments of the invention and are not therefore to be considered to limit the scope of the invention.

DETAILED DESCRIPTION OF THE INVENTION

Figure 1:
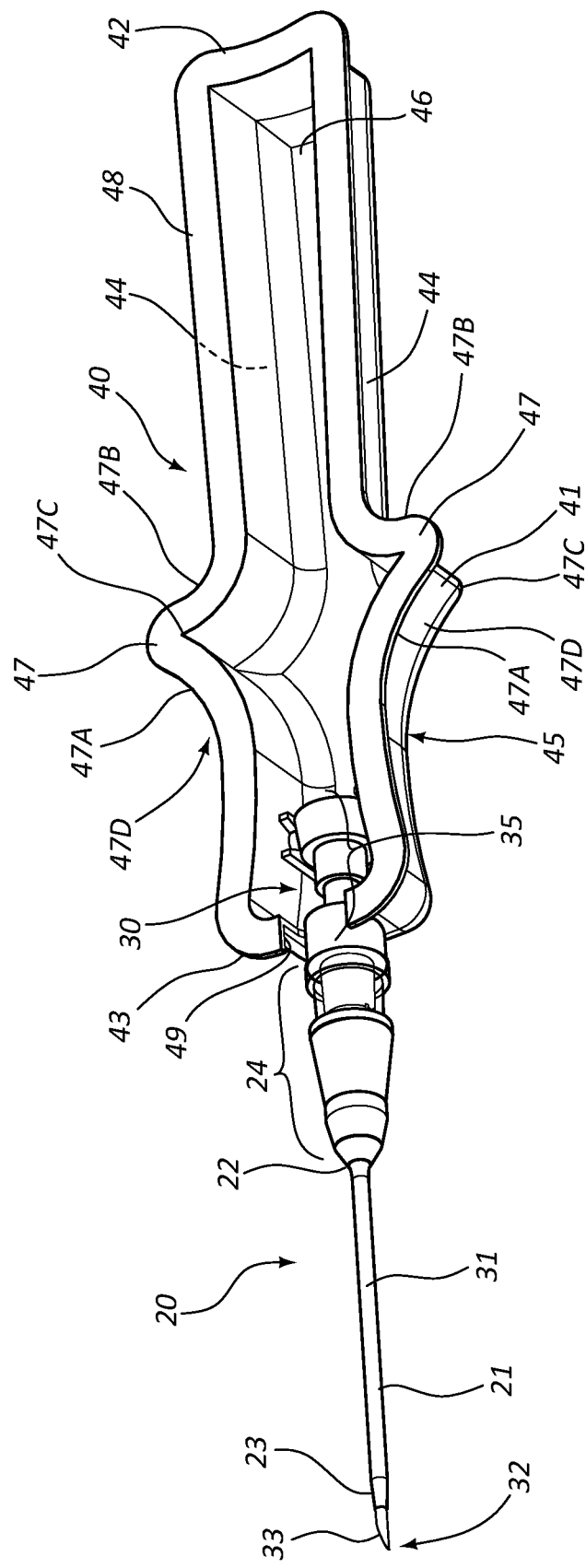
FIG. 1 is a perspective view of an integrated package and gripping device for a catheter in accordance with a representative embodiment of the present invention.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein, the term "proximal" refers to a location with respect to the device during normal use that is closest to the clinician and farthest from the patient. Conversely, the term "distal" refers to a location with respect to the device during normal use that is farthest from the clinician and closest to the patient. As used herein, the term "top", "up" or "upwardly" refers to a location with respect to the device during normal use that is radially away from the longitudinal axis of the device and away from the patient's skin. Conversely, as used herein, the term "bottom", "down" or "downwardly" refers to a location with respect to the device during normal use that is radially away from the longitudinal axis of the device and toward the patient's skin. As used herein, the term "in" or "inwardly" refers to a location with respect to the device during normal use that is toward the inside of the device. Conversely, as used herein, the term "out" or "outwardly" refers to a location with respect to the device during normal use that is toward the outside of the device.

As mentioned above, the present invention is described herein using like reference numbers for like elements in the different embodiments. It is to be understood that this invention is applicable to catheters having an integrated extension tube ("integrated catheters") as well as other catheters such as standard peripheral I.V. catheters. In addition, it is to be understood that this invention is applicable to catheter introducers and guidewire introducers and other medical devices that are designed to be inserted into a patient's vasculature using a standard over the needle insertion technique. Finally, while this invention is satisfied by embodiments in many different forms, there are shown in the drawings and herein described in detail, preferred embodiments of the invention with the scope of the invention measured by the appended claims.

Referring now to FIG. 1, an implementation of an integrated needle, catheter, and package grip assembly or device 10, in accordance with some embodiments of the present invention, is shown. As depicted in FIG. 1, according to various embodiments, assembly 10 generally includes a catheter assembly 20, an introducer needle assembly 30, and a package grip assembly 40. Each of the sub-assemblies 20, 30, and 40 will be discussed in greater detail below.

Catheter assembly 20 includes a catheter 21 that has a proximal end 22, a distal end 23 and a catheter adapter 24 connected or affixed to proximal end 22 of catheter 21. In some embodiments, catheter 21 defines a longitudinal lumen providing a fluid flow pathway there through. Catheter adapter 24 is affixed to proximal end 22 so as to maintain the fluid flow pathway defined by the longitudinal lumen of catheter 21. Suitable materials for catheter 21 include, but are not limited to, thermoplastic resins such as fluorinated ethylene propylene (FEP), polytetrafluoroethylene (PTFE), polyurethane and the like. Preferably, catheter 21 is formed from a thermoplastic hydrophilic polyurethane that softens with exposure to physiological conditions present in a patient's body (not shown). Suitable materials for catheter adapter 24 include, but are not limited to, thermoplastic polymeric resins such as polycarbonate, polystyrene, polypropylene and the like.

Figure 2:
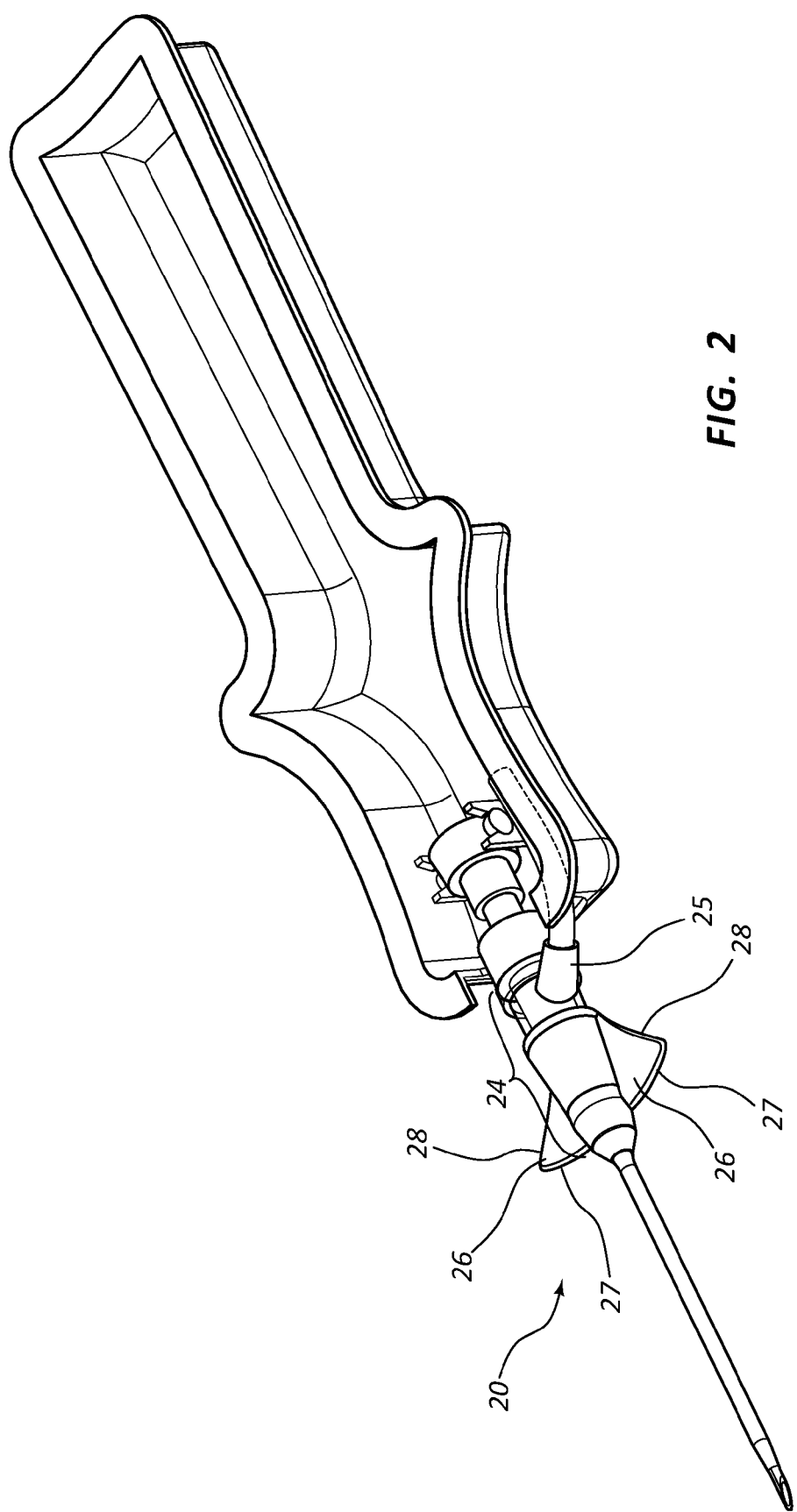
FIG. 2 is a perspective view of an integrated package and gripping device for a catheter in accordance with another representative embodiment of the present invention.

According to some embodiments, as shown in FIG. 2, catheter assembly 20 further includes an integrated extension port or tube 25 which extends from catheter adapter 24 and may include a fluid flow control device at its proximal end (not shown). In some embodiments, catheter assembly 20 also includes wings 26 which are attached to catheter adapter 24 and extend radially outward. Each wing includes a distal edge 27 and a proximal edge 28. Distal edge 27 is convex.

In some embodiments, catheter adapter 24 includes one or more integrated push tabs (not shown) or arms which extend radially from adapter 24 to facilitate placement of catheter 21 into a patient. According to some embodiments, the integrated push tab comprises a cantilever push tab. In various embodiments, the push tab includes various formations, such as ribbed gripping surfaces, to facilitate manual manipulation of the push tab. In still other embodiments, the push tab is ergonomically formed, such as to include concave surfaces adapted to facilitate comfort and ease of manual use for a clinician.

Figure 3:
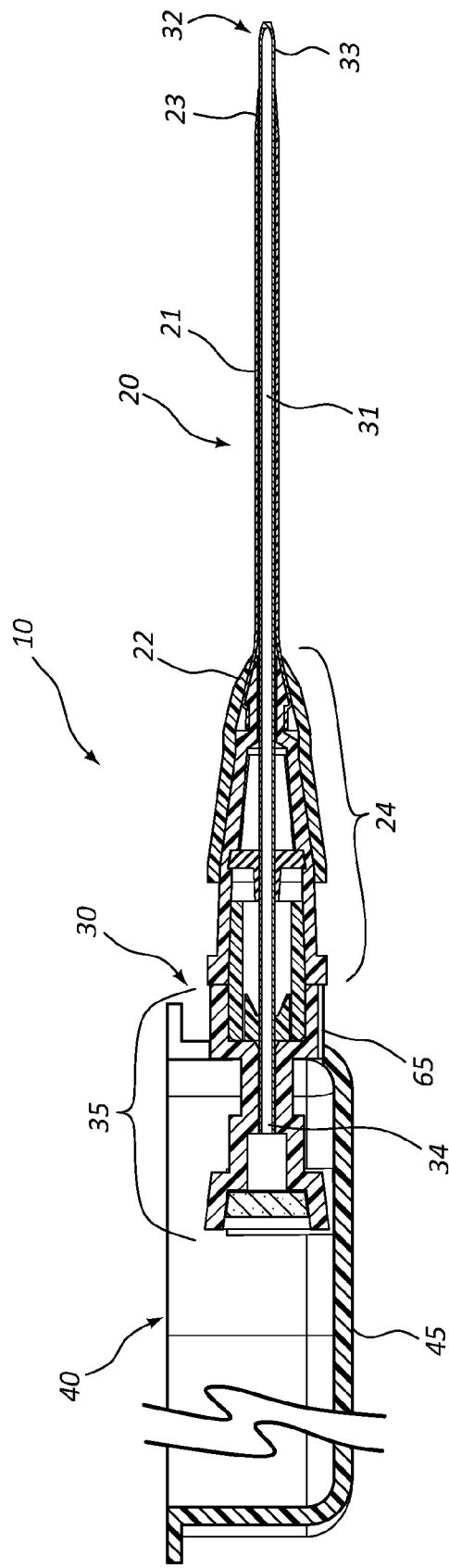
FIG. 3 is a side elevation view in cross section of an integrated package and gripping device for a catheter in accordance with a representative embodiment of the present invention.

With continued reference to FIG. 1, introducer needle assembly 30 includes introducer needle 31 having a sharp distal tip 32 defined by a bevel 33 and a proximal end 34 (see FIG. 3) connected or affixed to a needle hub 35. In some embodiments, introducer needle 31 defines at least a partial longitudinal lumen, which provides a fluid flow pathway through at least a portion of needle 31. In other embodiments, the lumen of needle 31 provides a fluid flow pathway there through. In some embodiments, a partial fluid flow pathway or lumen defined by needle 31 extends from distal tip 32 to a notch 36 (see FIG. 4) of needle 31. Introducer needle 31 is preferably formed from stainless steel and has a longitudinal axis that is generally parallel to the longitudinal axis of catheter assembly 20 and introducer needle assembly 30. In some embodiments, introducer needle 31 is replaceable with an introductory guidewire or other similar device sufficient to facilitate placement of catheter 21 or to otherwise provide sufficient structural support for the placement of catheter 21.

Figure 4:
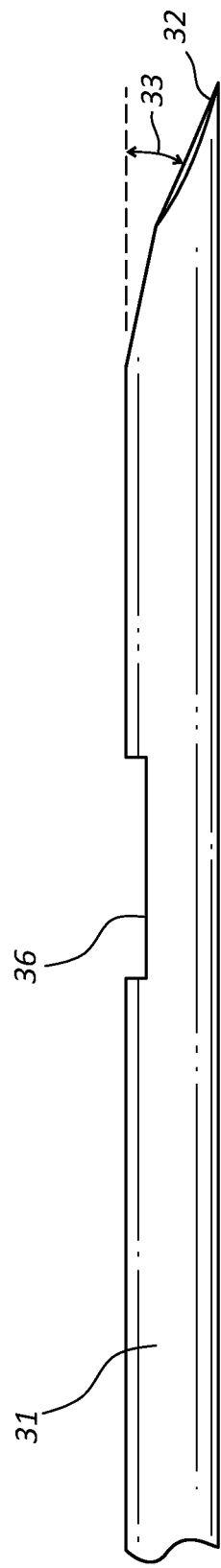
FIG. 4 is a side elevation view of an introducer needle of an integrated package and gripping device in accordance with a representative embodiment of the present invention.

According to some embodiments, as illustrated in FIG. 4, introducer needle 31 defines notch 36, i.e., an opening in the sidewall of introducer needle 31. In such embodiments, notch 36 allows fluid, such as blood, to flow into the distal open end 32 of introducer needle 31, through the at least partial lumen defined by needle 31, and through notch 36 into an annular space between introducer needle 31 and catheter 21. In other words, notch 36 provides a fluid communication pathway between the lumen defined by needle 31 and the lumen defined by catheter 21. The fluid can then flow through the fluid flow pathway defined by catheter 21 and catheter adapter 24 to allow the clinician to confirm successful venipuncture. This configuration allows the clinician easily to observe blood flashback along the distal portion 23 of catheter 21 and introducer needle assembly 30. In embodiments comprising an integrated extension port or tube 25, the clinician can further confirm successful venipuncture by observing blood flow into extension tube 25. Alternatively, needle hub 35 can include an integrated flashback chamber having an open proximal end. Where such a flashback chamber is used, a vented plug is located in the open proximal end of the flashback chamber to allow air to escape from the flashback chamber when blood enters the flashback chamber from introducer needle 31. Needle hub 35 may be formed from the same types of materials that are used to form catheter adapter 24. Of course, other materials could be used to form needle hub 35.

As illustrated, in some embodiments, catheter 21 is used with introducer needle assembly 30 and is coaxially and slidably disposed over introducer needle 31 with the distal end 23 of catheter 21 tightly engaging the outer surface of introducer needle 31. This configuration prevents peelback of catheter 21 and facilitates insertion of catheter 21 into a patient's blood vessel. In some embodiments, catheter 21 includes one or more chamfered surfaces at distal end 23 thereof. This configuration further prevents peelback of catheter 21 and facilitates insertion of the same into a patient's blood vessel. Prior to use, catheter 21 is slidably located about introducer needle 31 so that the sharp distal tip 32 of introducer needle 31 is distal of the distal end 23 of catheter 21. According to some embodiments, an internal septum (not shown) is disposed within the proximal end or opening of catheter assembly 20 and/or catheter adapter 24. In such embodiments, needle 31 extends through the septum prior to use of device 10. According to some embodiments, the internal septum disposed within the otherwise open proximal end of catheter adapter 24 forms a liquid barrier or seal upon removal of needle 31 therefrom.

With continued reference to FIG. 1, package grip assembly 40 generally includes a body 41 having a proximal end 42, a distal end 43, juxtaposing lateral sides or sidewalls 44, and a top 45, wherein body 41 defines a cavity 46. Body 41 doubles as both a package for storing and transporting the contents thereof (i.e., catheter assembly 20 and introducer needle assembly 30) as well as a grip, handle, or mechanical instrument for utilizing and placing catheter assembly 20 and introducer needle assembly 30.

Body 41 defining cavity 46 is shaped and sized such that is sufficiently large and has sufficient depth so as to be capable of fully housing catheter assembly 20 and introducer needle assembly 30 therein per various embodiments. According to some embodiments, the length and depth of body 41 is selected to provide a suitable gripping surface to device 10. For example, according to various embodiments, body 41 is configured to accommodate catheter assembly 20 and introducer needle assembly 30 when catheter 21 is coaxially disposed over introducer needle 31. In other embodiments, body 41 is configured to accommodate catheter assembly 20 and introducer needle assembly 30 when the two sub-assemblies are side-by-side therein. In still other embodiments, body 41 is configured to accommodate catheter assembly 20 and introducer needle assembly 30 wherein one or more of the two sub-assemblies includes additional features or elements, such as a port or tube 25, wings 26, and/or push tabs and the like. Body 41 may be formed from the same types of materials that are used to form catheter adapter 24 and/or needle hub 35. Of course, other materials could be used to form body 41. In various embodiments, body 41 is generally composed a rigid or semi-rigid polymer material having sufficient structural integrity so as to be capable of maintaining its general shape during normal use of device 10.

In various embodiments, body 41 is ergonomically shaped and includes wing formations or protrusions 47. Wing formations 47 are integrally formed in sidewalls 44 according to some embodiments. In other embodiments, however, wing formations 47 are attached to sidewalls 44. Wing formations 47 may be formed from the same types of materials that are used to form catheter adapter 24, needle hub 35, and/or body 41. Other materials could also be used to form wing formations 47. Each wing formation 47 includes a distal edge 47A and a proximal edge 47B. Distal edge 47A and proximal edge 47B are concave.

Wing formations 47 are formed to enhance the gripping surface of device 10. For example, in some embodiments, wing formation 47 on one side of device 10 is formed with an ergonomically shaped arête 47C configured or located so as to reside either between a user's index and middle finger tips, between a user's middle and ring finger tips, or between a user's ring and pinky finger tips during normal use of device 10. The opposing wing formation 47 is formed with an ergonomic concave surface at 47A designed to comfortably accommodate the naturally curved pad of the user's thumb. This configuration accommodates a comfortable and secure gripping surface by which device 10 can be manually manipulated and controlled during use.

In still other embodiments, sidewalls 44 and/or wing formations 47 further include gripping formations, such as grooves, bumps, ridges, or other outward surface textures to facilitate a user's grip of device 10 during use. According to various embodiments, body 41 is sized and shaped to enhance the manual dexterity of device 10. For example, the size of body 41 may be selected to ensure adequate control over the device by a desired grip. As another example, proximal end 42 of body 41 may be concave to enable a user to comfortably press a finger against the outward surface of proximal end 42 during use of device 10. In yet another example, sidewalls 44 of body 41 can include additional finger shaped grips formed therein or otherwise disposed along the length of lateral sides 44, which finger grips have a substantially ergonomic, concave, and/or oval shape.

In addition to the ergonomic features of body 41 discussed above, some embodiments further include a flange or lip 48 disposed around all or part of the bottom perimeter of body 41. Flange 48 is integrally formed with body 41 according to some embodiments. In other embodiments, however, flange 48 is attached to the bottom perimeter of body 41. Flange 48 may be formed from the same types of materials that are used to form catheter adapter 24, needle hub 35, and/or body 41. Other materials could also be used to form flange 48.

According to some embodiments, wing formations 47 and/or flange 48 is/are configured so as to encourage a user's proper grip and the proper orientation of device 10 during use. For example, in some embodiments, flange 48 extends a sufficient length perpendicular from sidewalls 44 such that device 10 is uncomfortable to inadvertently grasp upside down or incorrectly. Similarly, wing formations 47 are configured to comfortably accommodate the natural curvature of a user's finger tips or pads when device 10 is properly oriented. This configuration encourages a user to grip device 10 in a specifically intended way so as to orient catheter assembly 20 and introducer needle assembly 30 for proper insertion into a patient's vasculature.

Various structural enhancing features of body 41 are contemplated herein. For example, in some embodiments, the integral formation of wings 47 with an arête 47C in sidewalls 44 has the added advantage of increasing the structural integrity of body 41. Similarly, the structural integrity of body 41 is further enhanced by the formation of the integral flange or lip 48 around all or part of the bottom perimeter of body 41 according to some embodiments. In still other embodiments, bullnose corners, chamfered corners, and/or convex or concave surfaces are employed at various locations of body 41 so as to simultaneously enhance the structural integrity thereof while providing an ergonomic configuration suitable to a user's grip.

Figure 5:
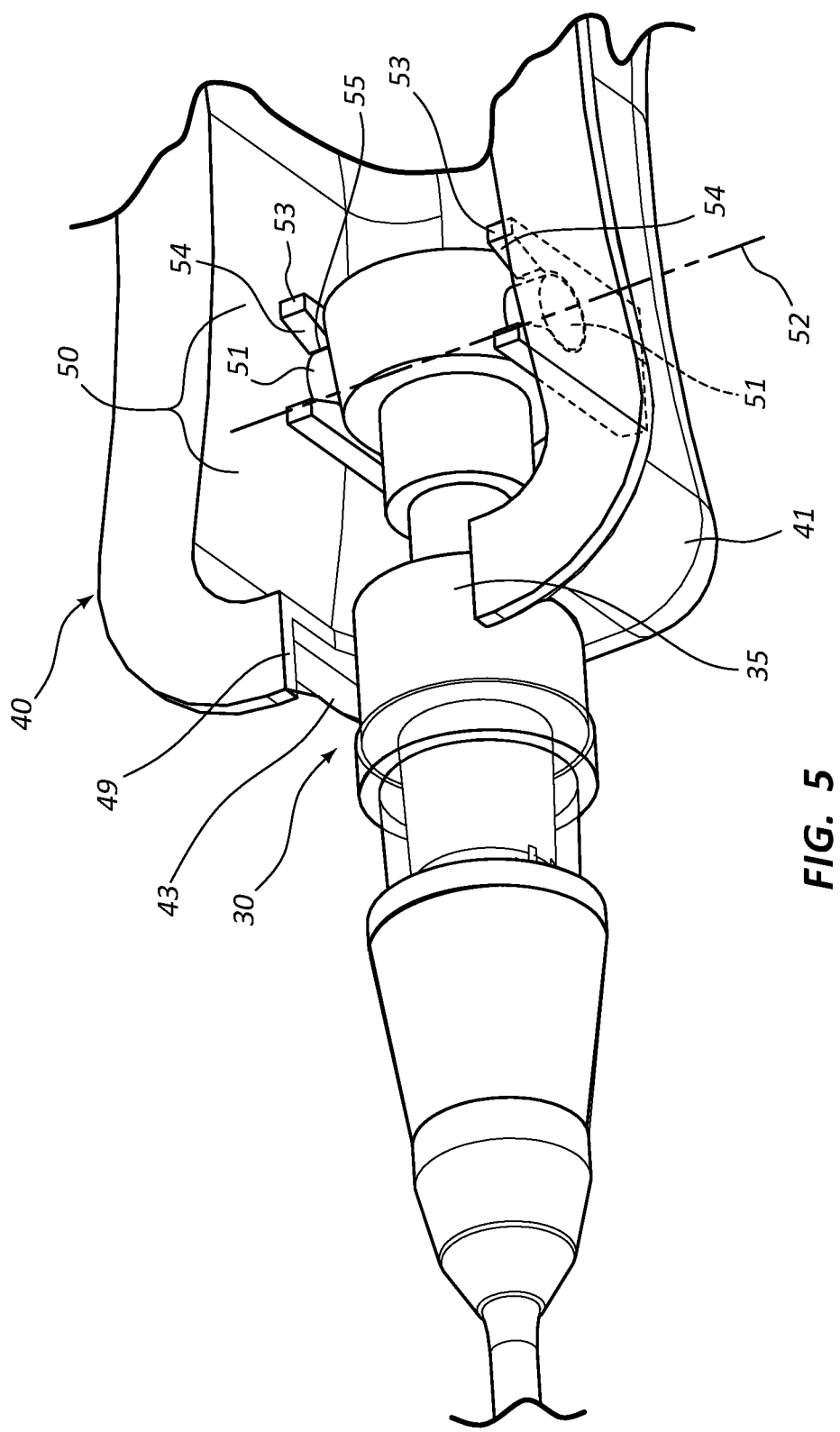
FIG. 5 is a perspective view of a hinge coupling assembly of an integrated package and gripping device in accordance with a representative embodiment of the present invention.
Figure 6:
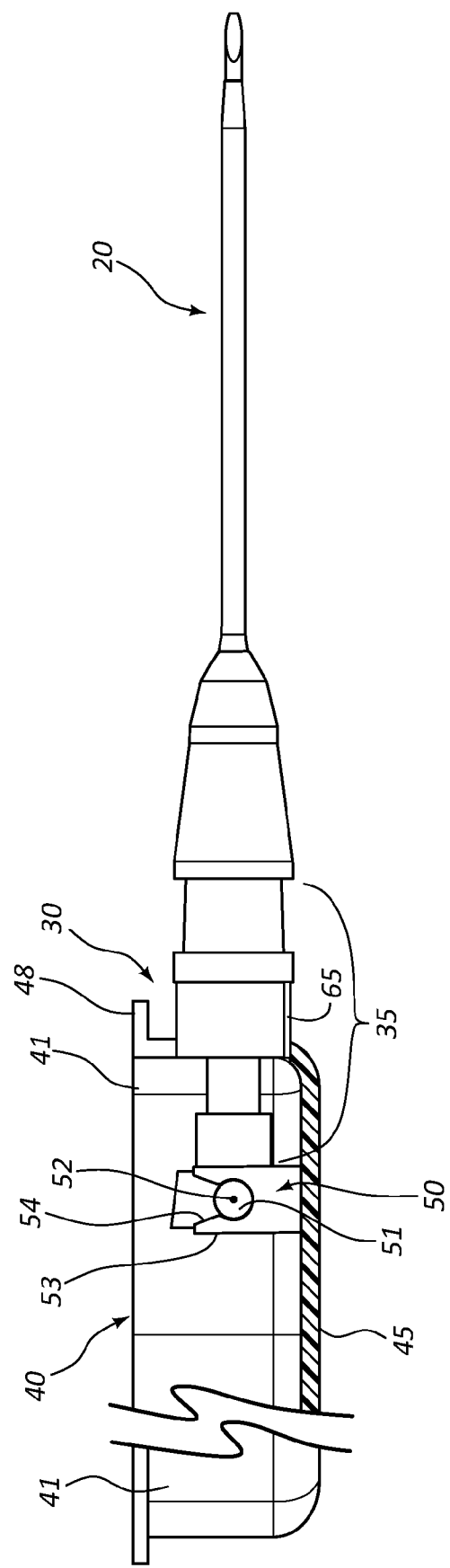
FIG. 6 is another side elevation view in cross section of an integrated package and gripping device for a catheter in accordance with a representative embodiment of the present invention.

In some embodiments, device 10 further includes a hinge coupling assembly 50 for hingedly coupling introducer needle assembly 30 to package grip assembly 40. For example, as illustrated in FIGS. 5 and 6, in some embodiments, a proximal end of needle hub 35 includes an integrally formed axle or set of axle bosses 51 defining a rotational axis 52. In such embodiments, the distal end 43 of body 41 includes corresponding matting clips or cradles 53. Cradles 53 are generally located proximate the distal portion of body 41 proximal relative to distal end 43. Bosses 51 and cradles 53 are designed and sized to mattingly engage such that cradles 53 retain axle bosses 51 against lateral and longitudinal displacement while simultaneously permitting bosses 51 to rotate about axis 52. In some embodiments, cradles 53 define chamfered openings 54 such that bosses 51 can be "snapped" into place during the manufacturing process and retained in the manner described above during subsequent use. In such embodiments, chamfered openings 54 are sized so as to be sufficiently smaller than the diameter of axel bosses 51 such that axel bosses 51 are capable of being forced beyond an internal edge 55 of chamfered openings 54 thereby slightly bending or temporarily displacing the material of cradles 53 sufficient to permit axel bosses 51 to pass through chamfered openings 54 and be retained in a rotatable position once cradles 53 resume their initial orientation.

Those of skill in the art will appreciate that a variety of mating hinge configurations or other hinge coupling assemblies may be employed without departing from the structures, methods, or other essential characteristics as broadly described herein. For example, in some embodiments, cradles 53 are substantially solid having depressions or shallow cavities partially formed therein. In such embodiments, the depressions correspondingly mate with rounded bumps or protuberances formed on the proximal end of needle hub 35, wherein the protuberances define the axis of rotation 52. In such embodiments, cradles 53 are displaced laterally relative to the longitudinal axis of body 41 during the assembly of device 10 until the protuberances formed on the proximal end of needle hub 35 slip past the upward edge of cradles 53 and rotatably seat in the depressions.

In the various embodiments contemplated herein, mating hinge mechanisms 51 and 53 may be formed from the same types of materials that are used to form catheter adapter 24, needle hub 35, body 41, and/or wing formations 47. Other materials could also be used to form mating hinge mechanisms 51 and 53. Materials are selected to provide sufficient structural integrity for use of device 10 while allowing cradles 53 to displace as necessary during the manufacturing process and then to return under biasing memory to their initial orientation and to maintain such initial orientation during normal use. In addition, materials are selected to enable the manufacture of mating surfaces between hinge mechanisms 51 and 53 which facilitate rotation of mechanism 51 without undue friction or resistance. In some embodiments, however, some rotational resistance or friction between hinge mechanisms 51 and 53 is desirable so as to encourage the components of device 10 to maintain a specific orientation relative to one another. For example, according to some embodiments, it is desirable to have sufficient rotational resistance between hinge mechanisms 51 and 53 such that, prior to use, introducer needle assembly 30 is encouraged not to rotate relative to package grip assembly 40 until the user desires and initiates such rotation. In other embodiments, however, gravity is used to cause the rotation of introducer needle assembly 30 relative to package grip assembly 40. In such embodiments, it is desirable to minimize or reduce rotational resistance or friction between hinge mechanisms 51 and 53 so as to permit substantially free rotation of introducer needle assembly 30 relative to package grip assembly 40.

With further reference to FIG. 5, some embodiments include an opening 49 defined by and at the distal end 43 of body 41. In such embodiments, introducer needle assembly 30 extends through body 41 at opening 49 when introducer needle assembly 30 is activated or otherwise positioned for insertion into a patient's vasculature.

In some embodiments, device 10 further includes a sealing label or cover 60 having a proximal end 61 and a distal end 62. (See FIGS. 7A-7B.) The sealing label or cover ensures the sterility of catheter assembly 20 and introducer needle assembly 30 prior to activation and use of device 10 and prevents foreign contaminants from interacting with the internal contents of package grip assembly 40 prior to use of device 10. In such embodiments, the sealing cover is removably affixed or temporarily attached to the bottom of body 41 at or adjacent flange or lip 48. In this way, the sealing label is attached around all or part of the bottom perimeter of body 41. In further embodiments, the sealing label or cover is also configured to extend and fold over distal end 43 of body 10 so as to sealably cover opening 49 prior to removal of the sealing label. The sealing label or cover may be removably affixed to flange or lip 48 and/or over opening 49 by any appropriate means known and common to those of skill in the art, such as via adhesive or glue.

In some embodiments having a hinge coupling assembly 50 as described above, the sealing label or cover can also be removably affixed or temporarily attached to a surface or point 65 (see FIGS. 3, 6 and 7C) located on the top of introducer needle assembly 30. This configuration enables the sealing label or cover to double as mechanism for activating device 10 upon removal of the sealing label as discussed in greater detail below.

In embodiments having a removable sealing label or cover, arête 47C is rounded or has a gradually radiused extremity. This configuration enables the sealing label or cover to be removed in order to activate and use device 10 while minimizing or reducing instances of the sealing label or cover tearing undesirably as the sealing label or cover is removed adjacent wing formations 47. Wing formations 47 can be formed with a variety of radiused curvatures at 47A, 47B, 47C and 47D so as to encourage removal of the sealing label or cover in a manner that minimizes or reduces instances of the sealing label or cover tearing undesirably during removal.

Figure 7A:
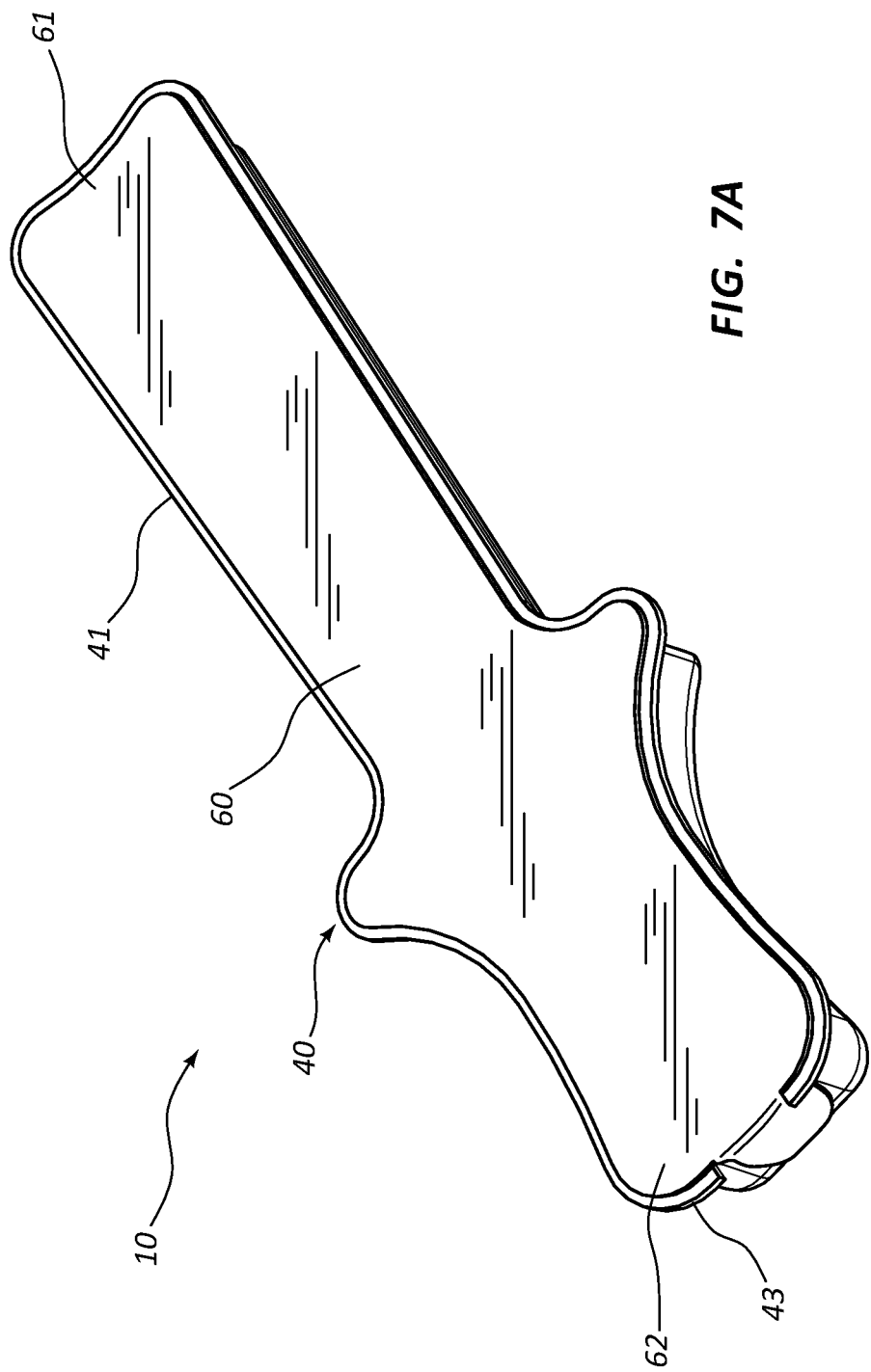
FIG. 7A is perspective view of an integrated package and gripping device for a catheter having a sealing label or cover in accordance with a representative embodiment of the present invention.
Figure 7B:
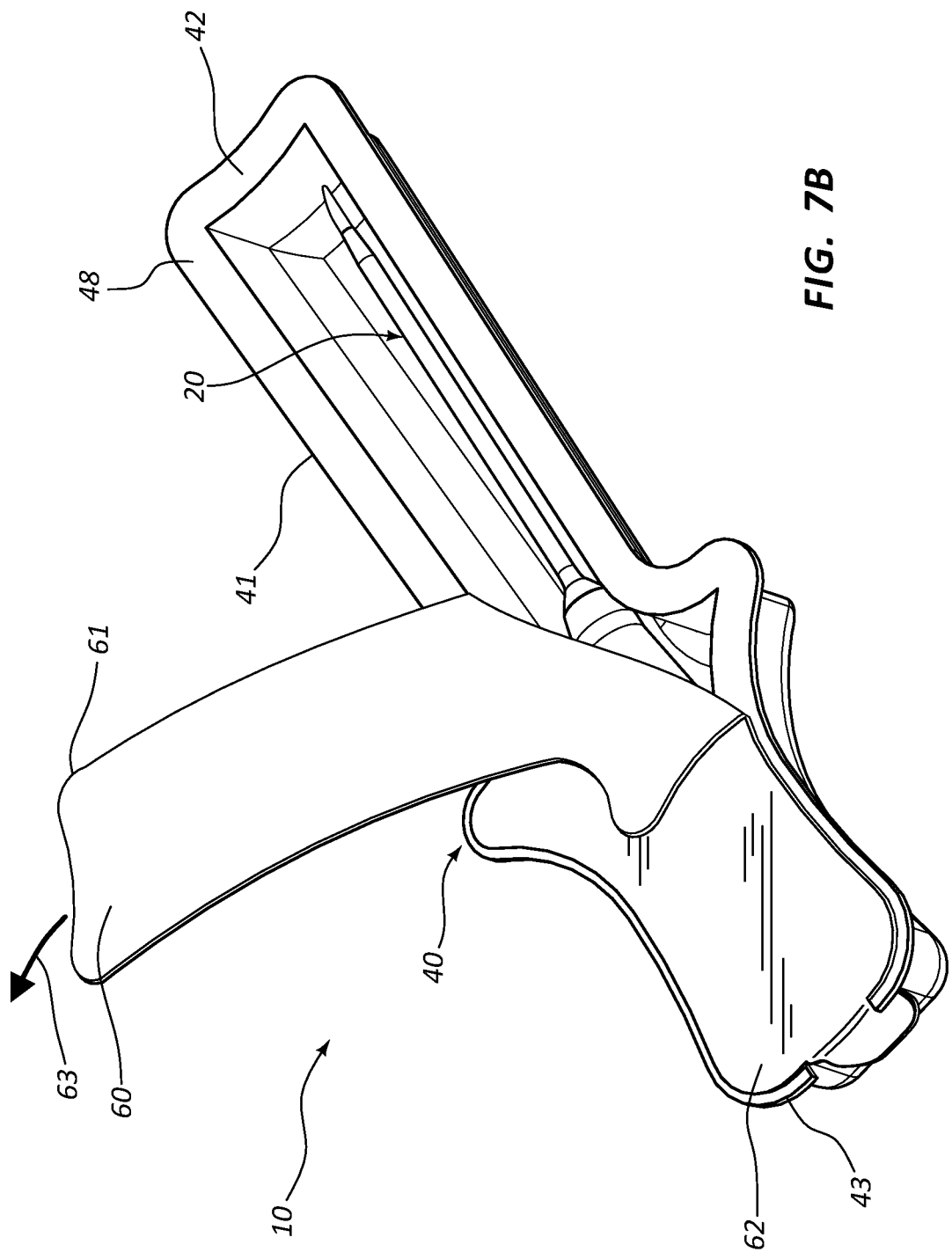
FIG. 7B is perspective view of the device of FIG. 7A with the sealing label or cover partially removed in accordance with a representative embodiment of the present invention.

With reference to FIGS. 7A through 7E, the activation of device 10 according to some embodiments is illustrated. As depicted in FIG. 7A, according to some embodiments, device 10 initially includes sealing label or cover 60. As discussed above, sealing label or cover 60 sealingly covers the cavity 46 defined by body 41 and sterilely encloses catheter assembly 20 and introducer needle assembly 30 within package grip assembly 40 prior to activation. In some embodiments, sealing label or cover 60 also covers opening 49. Prior to activation, according to some embodiments, catheter assembly 20 and introducer needle assembly 30 are contained within the cavity 46 of package grip assembly 40 as illustrated in FIG. 7B.

With continued reference now to FIG. 7B, device 10 is activated as a user (not shown) grips the proximal end 61 of label 60 and lifts or applies a lateral force thereto outwardly in a general direction 63. In some embodiments, label 60 includes a tab, flap, stub, strip, fold, or tailpiece (not shown) that facilitates the user's grasp of proximal end 61 of label 60. In such embodiments, the tab, flap, stub, strip, fold, or tailpiece is long enough to be easily gripped and pulled on by the user so as to overcome the adhesive seal between label 60 and flange 48 to thereby remove label 60. According to some embodiments, the proximal end 61 of label 60 is longer than the proximal end 42 of body 41 such that proximal end 61 overhangs or is distal proximal end 42. In this configuration, proximal end 61 itself doubles as a suitable tab, flap, stub, strip, fold, or tailpiece that facilitates the user's grasp and removal of label 60.

Figure 7C:
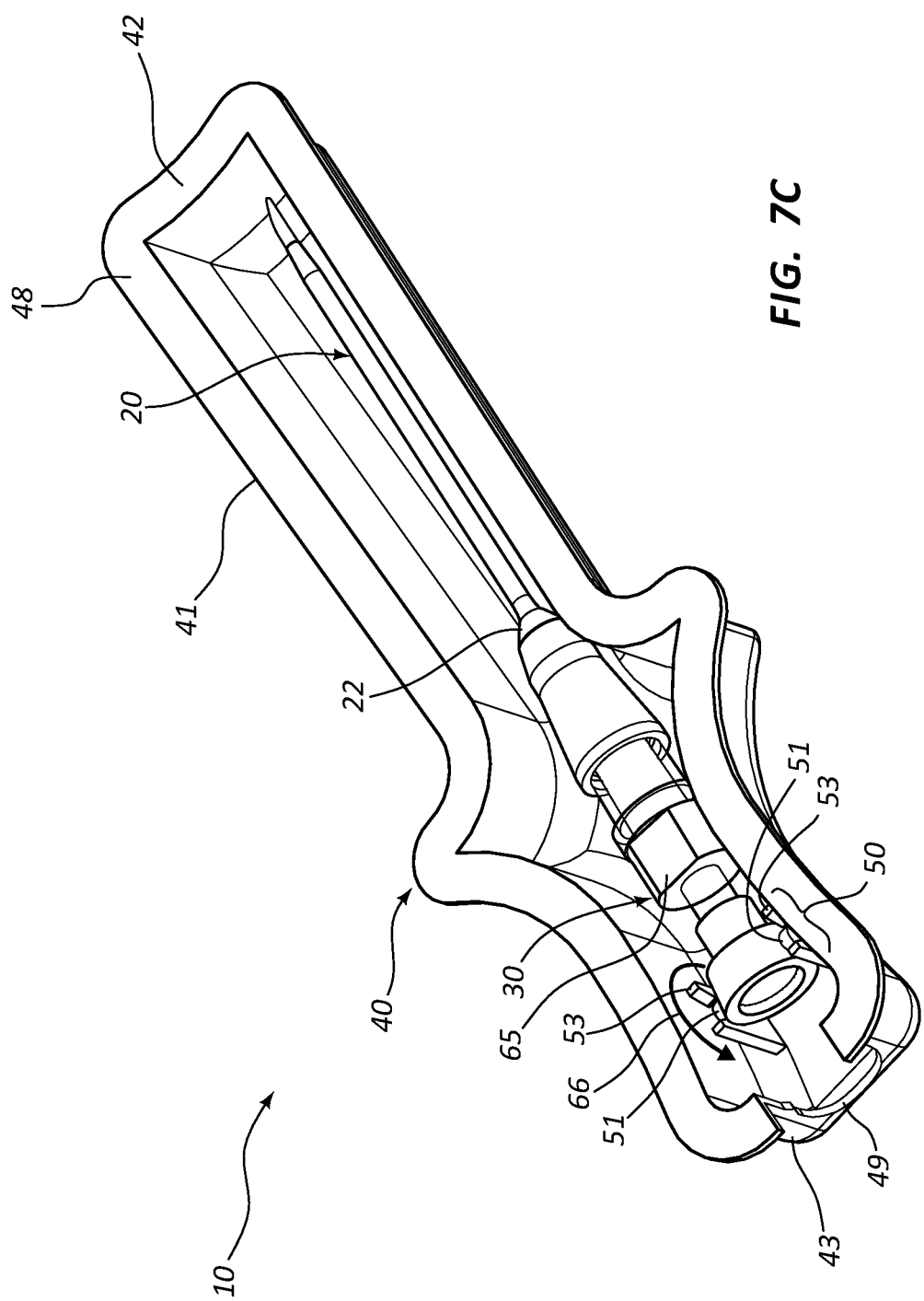
FIG. 7C is perspective view of the device of FIG. 7A with the sealing label or cover fully removed, the device occupying a closed position, in accordance with a representative embodiment of the present invention.
Figure 7D:
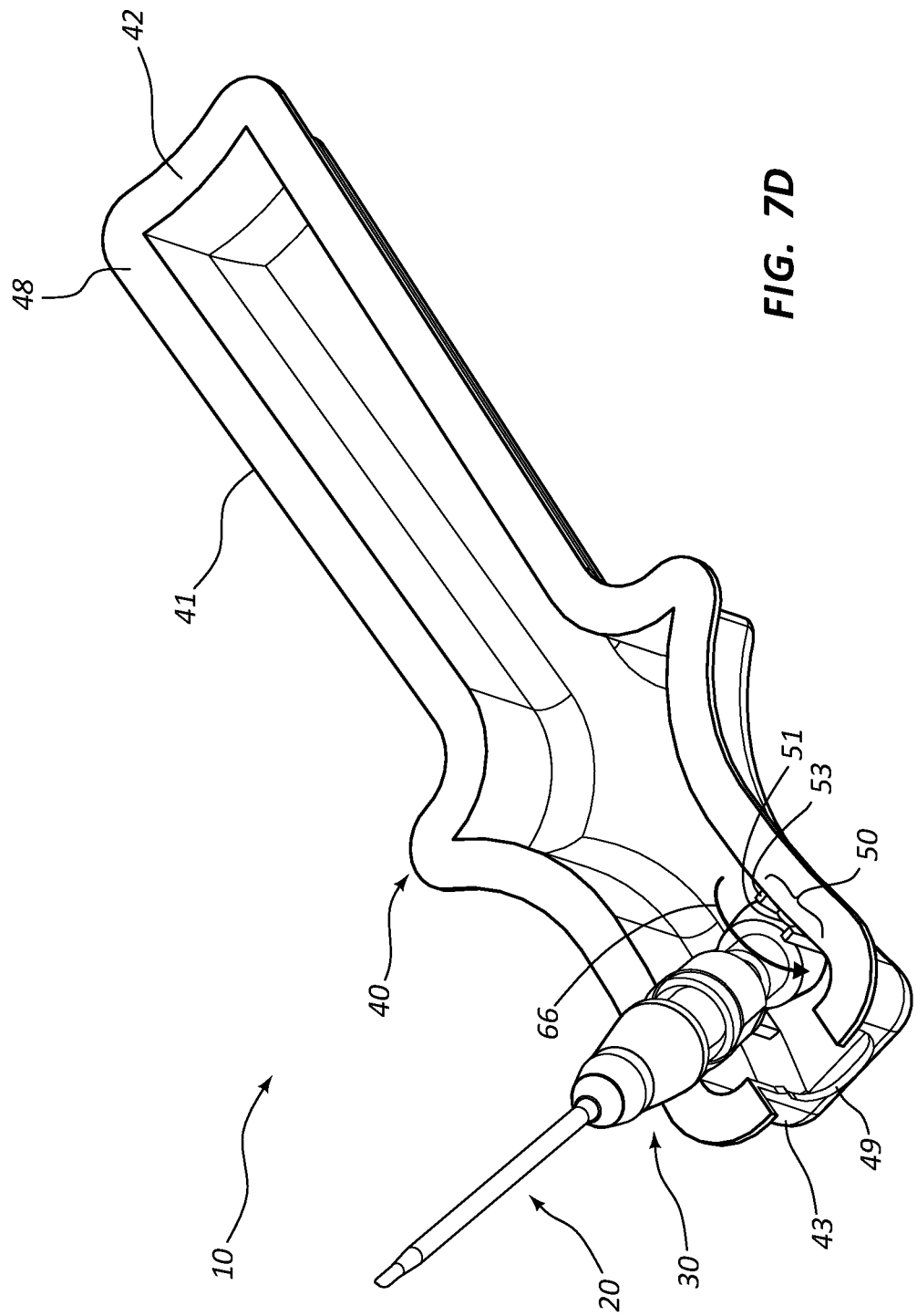
FIG. 7D is perspective view of the device of FIG. 7A wherein the catheter and introducer needle sub-assemblies are depicted in transition between an open and a closed position in accordance with a representative embodiment of the present invention.

Still with reference to FIG. 7B, the user continues to activate device 10 as label 60 is fully removed via force 63 starting proximally and continuing distally until label 60 is fully removed from device 10 as depicted in FIG. 7C. According to some embodiments, as illustrated in FIG. 7C, label 60 is fully removed and additional steps are yet required to fully activate device 10, including rotating introducer needle assembly 30 and catheter assembly 20 in a direction 66 via hinge coupling assembly 50 until a proper orientation of introducer needle assembly 30 and catheter assembly 20 is achieved for insertion thereof into a patient's vasculature. (See FIGS. 7D and 7E.)

According to various embodiments, introducer needle assembly 30 and catheter assembly 20 can be rotated in a direction 66 to achieve proper orientation thereof by a variety of methods and associated mechanisms. For example, in some embodiments, following the partial or complete removal of label 60, device 10 is inverted such that introducer needle assembly 30 and catheter assembly 20 rotate via hinge coupling assembly 50 in the direction 66 under the force of gravity. By way of another example, introducer needle assembly 30 and/or catheter assembly 20 include a thumb tab (not shown), such as a cantilevered tab, facilitating the manual rotation thereof in direction 66. In still other embodiments, hinge coupling assembly 50 includes a biasing spring (not shown). As label 60 is removed, the biasing spring supplies the moment or rotational force 66 necessary and sufficient to properly position introducer needle assembly 30 and catheter assembly 20 for insertion thereof into a patient's vasculature. In still other embodiments, the biasing spring is activated by a push-button mechanism (not shown) such that upon removal of label 60 the user may then activate the biasing spring via the push-button mechanism such that introducer needle assembly 30 and catheter assembly 20 are rotated in the direction 66 under force supplied by the biasing spring until a final proper orientation is achieved. In this way, introducer needle assembly 30 and catheter assembly 20 remain safely housed within package grip assembly 40 until the biasing spring is manually activated.

In other embodiments, label 60 is removably affixed or temporarily attached to a surface 65 (see FIG. 7C). Surface 65 can be located at any suitable location on catheter assembly 20 and/or introducer needle assembly 30 between the proximal end 22 of catheter 21 and hinge coupling assembly 50 so long as surface 65 occupies the same general plane as flange 48. In such embodiments, the moment or rotational force 66 necessary and sufficient to properly position introducer needle assembly 30 and catheter assembly 20 for insertion thereof into a patient's vasculature is generated and applied as label 60 is removed as previously described. In such embodiments, an adhesive is chosen to provide enough bond strength between label 60 and surface 65 such that, upon removal, label 60 will pull introducer needle assembly 30 and catheter assembly 20 into the proper orientation for use but then predictably fail or yield such that label 60 can be fully removed from device 10. This configuration permits the user to simultaneously remove label 60 and fully activate device 10 for subsequent use as removal of label 60 also rotates introducer needle assembly 30 and catheter assembly 20 into the proper orientation for insertion thereof into the patient's vasculature.

Figure 7E:
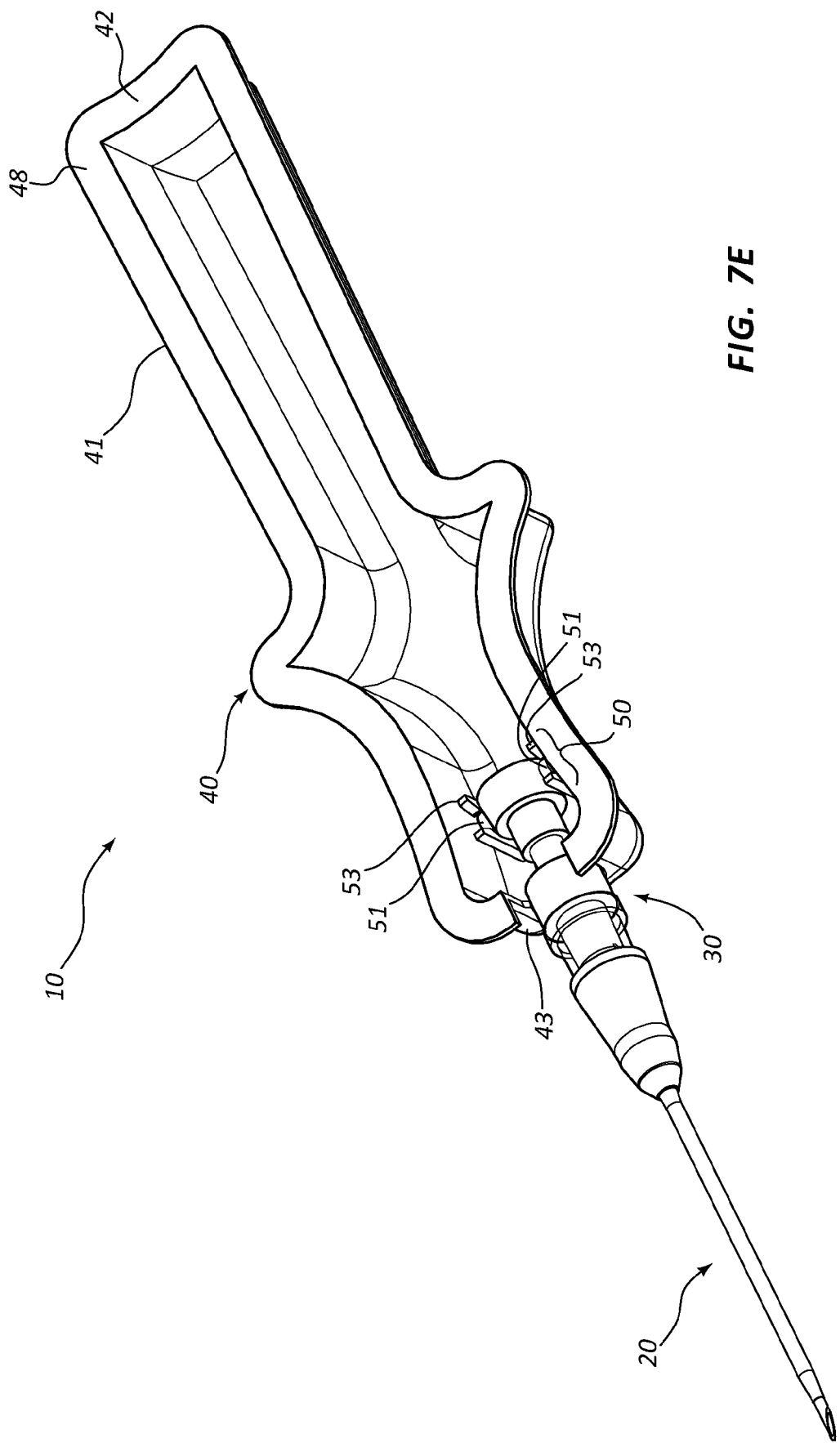
FIG. 7E is perspective view of the device of FIG. 7A with the device occupying an open position and ready for use in accordance with a representative embodiment of the present invention.

According to some embodiments, device 10 is configured so as to be biased in either a first, inactive, "closed" position (e.g., FIG. 7C) or a second, active, "open" position (e.g., FIG. 7E). For example, as depicted in FIG. 7C, the first, inactive or closed position corresponds with catheter assembly 20 and introducer needle assembly 30 being contained within package grip assembly 40. As depicted in FIG. 7E, on the other hand, the second, active, or open position corresponds with catheter assembly 20 and introducer needle assembly 30 extending longitudinally through body 41 at opening 49 so as to be positioned for insertion into a patient's vasculature.

As mentioned above, according to some embodiments, device 10 is biased in either the closed or the open position. In some embodiments, hinge coupling assembly 50 includes or comprises such biasing mechanisms 70. For example, in some embodiments, as depicted in FIG. 8A, axel bosses 51 are generally elliptical in shape. In such embodiments, the major axis 71 of the elliptical axel boss 51 is perpendicular to the top and bottom of device 10 and the minor axis 72 of the elliptical axel boss 51 is parallel to the top and bottom of device 10 when device 10 is in either the closed or the open position. As catheter assembly 20 and introducer needle assembly 30 are rotated via hinge coupling assembly 50 between the closed and open positions, the antipodal points of elliptical axel bosses 51 temporarily push against cradles 53 thereby slightly bending or temporarily displacing the material of cradles 53 sufficient to permit elliptical axel bosses 51 to rotate about axis of rotation 52 in the direction 67. Once the antipodal points of elliptical axel bosses 51 are rotated more than ninety degrees (90°), the biasing memory of cradles 53 pushes back against elliptical axel bosses 51 until the original shape and orientation of cradles 53 is resumed thereby biasing device 10 in either the open or closed position.

Figure 8B:
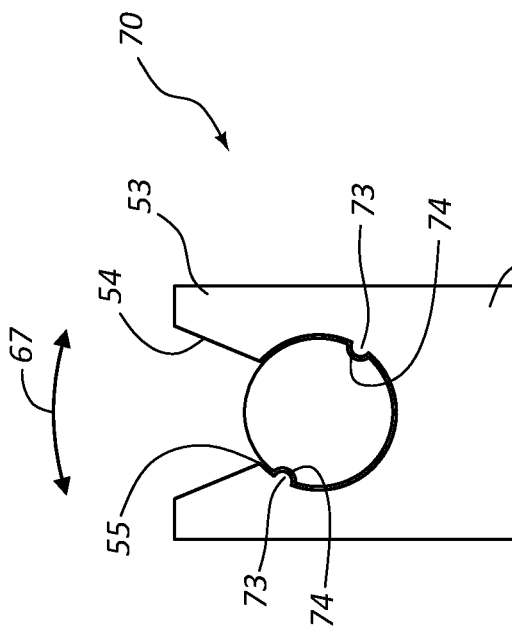
FIG. 8B is a side elevation view of another hinge coupling assembly according to another representative embodiment of the present invention.
Figure 8D:
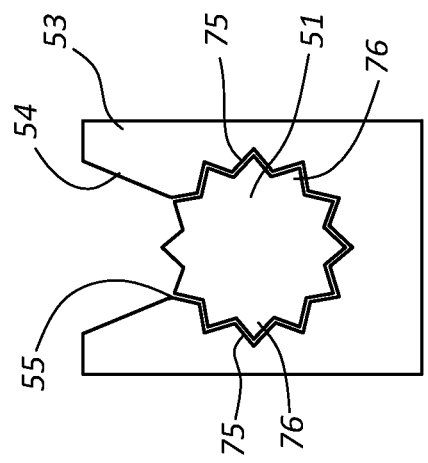
FIG. 8D is a side elevation view of a another hinge coupling assembly according to still another representative embodiment of the present invention.
Figure 8A:
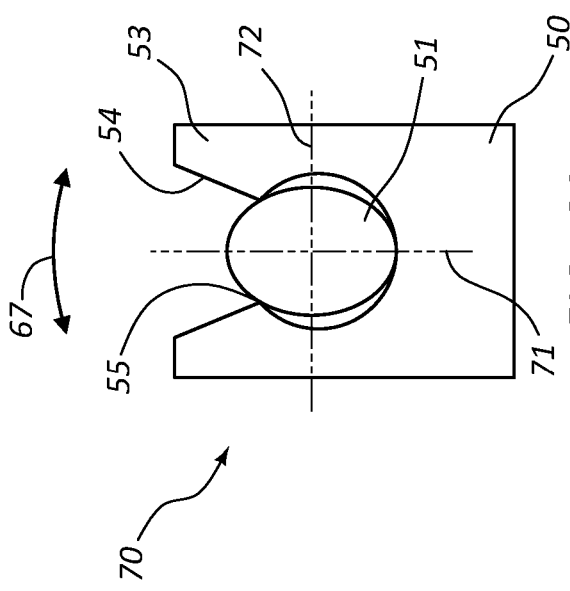
FIG. 8A is a side elevation view of a hinge coupling assembly of an integrated package and gripping device in accordance with a representative embodiment of the present invention.
Figure 8C:
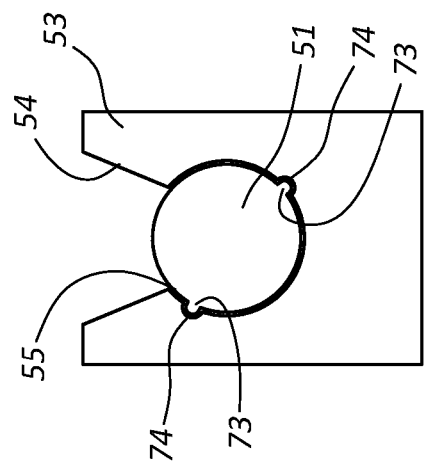
FIG. 8C is a side elevation view of another hinge coupling assembly according to yet another representative embodiment of the present invention.

Various non-limiting alternative embodiments are depicted in FIGS. 8B through 8D. As shown in FIG. 8B, cradles 53 include bumps, protrusions, or protuberances 73 which correspond with cavities, voids, or depressions 74 formed in bosses 51. FIG. 8C depicts an alternative configuration wherein protuberances 73 are included on bosses 51 while depressions 74 are formed in cradles 53. Still other embodiments are depicted in FIG. 8D, wherein bosses 51 include alternating chamfered surfaces 76 disposed about the external lateral perimeter thereof and cradles 53 include corresponding alternating internal chamfered surfaces 75. In still other embodiments, biasing springs (not show) in concert with tab and notch formations (not show), push-button activation mechanisms (not shown), and/or "snap-fit" features (not shown) are also contemplated for biasing device 10 in either the open or closed positions as desired.

In still other embodiments, removably interlocking components are included elsewhere within the structure of device 10 for biasing device 10 in either the open or closed positions as desired. For example, in some embodiments, needle hub 35 includes interlocking external mating mechanisms, such as openings, slots, cavities, depressions, voids, bumps, tabs, or protrusions which correspond with mating formations included on package grip assembly 40, such as adjacent opening 49 or elsewhere. In this manner, when device 10 is in the closed position, the corresponding interlocking components associated with the closed position bias, lock, or retain catheter assembly 20 and introducer needle assembly 30 within package grip assembly 40. When device 10 is transitioned to the open position, the bond or coupling force between the closed position interlocking components is overcome and the corresponding interlocking components associated with the open position are engaged thus biasing, locking, or retaining catheter assembly 20 and introducer needle assembly 30 in the open position. The foregoing process is reversible following use of device 10 so as to once again bias catheter assembly 20 and introducer needle assembly 30 within package grip assembly 40 for disposal.

The present invention may be embodied in other specific forms without departing from its structures, methods, or other essential characteristics as broadly described herein and claimed hereinafter. By way of example, in some embodiments, package grip assembly 40 includes an integrally formed bottom (not shown) formed of thermoplastic polymeric resins such as polycarbonate, polystyrene, polypropylene and the like consistent with body 41. In such embodiments, the bottom of package grip assembly 40 covers cavity 46 defined by body 41 at the bottom thereof. According to some embodiments, package grip assembly 40 further includes internal slots, pathways, or guide tracks (not shown) which correspond to sliding structural tabs, pins, or protrusions (not shown) formed adjacent the proximal end of needle hub 35. This configuration permits catheter assembly 20 and introducer needle assembly 30 to slide in and out of package grip assembly 40 at opening 49 via interaction between the sliding components and corresponding guide tracks. According to some embodiments, the internal slots, pathways, or guide tracks and corresponding structural tabs, pins, or protrusions collectively comprise a sliding guide track coupling assembly between package grip assembly 40 and introducer needle assembly 30. In such embodiments, the device is activated or otherwise transitioned from a closed position to an open position via the sliding guide track assembly.

In some embodiments, catheter assembly 20 and introducer needle assembly 30 are spring loaded such that device 10 is transitioned to an active use, or open, position by biasing spring force. A push-button activation mechanism is contemplated in connection with some embodiments. In other embodiments, however, catheter assembly 20 and introducer needle assembly 30 are manually transitioned to an open position. For example, in some embodiments, a thumb push tab affixed to needle hub 35 extends through body 41 such that catheter assembly 20 and introducer needle assembly 30 can be pushed into an open orientation via the push tab and subsequently retracted into a closed position by the same push tab. In still other embodiments, catheter assembly 20 and introducer needle assembly 30 are reverse spring loaded such that device 10 is transitioned to an active use, or open, position by manual force and, following use of device 10, catheter assembly 20 and introducer needle assembly 30 are automatically retracted into a closed position by biasing spring force.

In yet additional embodiments, catheter assembly 20 and introducer needle assembly 30 are withdrawn from cavity 46 through opening 49 via removal of a sealing label sterilely covering opening 49 prior to activation of device 10. In such embodiments, an adhesive is chosen to provide enough bond strength between the label and a surface of introducer needle assembly 30 such that, upon removal, the label will pull introducer needle assembly 30 and catheter assembly 20 through opening 49 and into an open position for use but then predictably fail or yield such that the label can be fully removed from device 10 so as not to interfere with the subsequent use thereof. This configuration permits the user to simultaneously remove the label and fully activate device 10 for subsequent use as removal of the label also pulls introducer needle assembly 30 and catheter assembly 20 into the proper position for insertion thereof into the patient's vasculature. The various biasing or locking features described above are also contemplated in connection with the foregoing embodiments such that device 10 is biased or retained in either the open or closed positions as desired.

In some embodiments, device 10 further includes either an active or a passive sharps injury protection feature (not shown) to protect the clinician from the contaminated needle point 32 and needle stick injuries. For example, in some embodiments, a sharps injury protection feature defining an internal cavity, such as a shield or shroud (not shown), is longitudinally disposed between needle hub 35 and catheter adapter 24. The internal cavity defined by the shroud includes a proximal opening and a distal opening in communication therewith. This configuration allows introducer needle 31 to extend longitudinally through the shroud housing. The shroud further includes an internal lock that prevents unwanted proximal and distal movement of sharp distal tip 32 of introducer needle 31 out of the distal end of the needle shield once sharp distal tip 32 has been proximally withdrawn into the needle shield. Such a lock can take many forms as known to those of skill in the art. Following use of device 10, needle 31 is withdrawn from catheter 21 and through the sharps protection shroud until needle tip 32 is enclosed and locked or retained within the sharps protection shroud. The introducer needle assembly 30, including the sharps protection shroud, are then disconnected from the catheter adapter 24 for disposal. Those of skill in the art will appreciate the variety of active or a passive sharps injury protection features which may be employed in connection with the present invention.

In other embodiments, package grip assembly 40 doubles as a sharps protection shuttle. In such embodiments, following placement of catheter assembly 20 within a patient, introducer needle assembly 30 is withdrawn from the patient and catheter assembly 20 via package grip assembly 40 and introducer needle assembly 30 is then folded into or otherwise withdrawn into a closed position wherein it is contained within package grip assembly 40. This configuration protects the clinician from the contaminated needle point 32 and needle stick injuries even where a separate sharps injury protection feature is not included with device 10.

The introducer needle assembly 30, in concert with the package grip assembly 40, is generally used to facilitate insertion of the integrated catheter assembly 20 into a patient. The various configurations and embodiments described above allow a clinician to insert catheter 21 using a number of different techniques. Such techniques include, but are not limited to, a single handed technique that may be used for inserting ported catheters, a single handed technique that may be used for inserting a straight catheter, and various two handed techniques.

According to some embodiments, in order to place catheter 21 into a patient's blood vessel, the clinician activates or opens device 10 as generally described with reference to FIGS. 7A through 7E or elsewhere above. In this way, device 10 is opened or activated such that catheter assembly 20 is oriented and positioned for insertion into a patient's vasculature. Following activation of device 10, the clinician substantially longitudinally aligns introducer needle 31 and catheter 21 with the target blood vessel. In some embodiments, bevel 33 of sharp distal tip 32 should be facing substantially away from the patient's skin surface during venipuncture. In other embodiments, bevel 33 of sharp distal tip 32 should be facing either the left or the right side of the target blood vessel during venipuncture. The clinician inserts introducer needle 31 and catheter 21 at a shallow angle, preferably less than about 35 degrees (35°), into the patient's skin so that sharp distal tip 32 enters the target blood vessel. The clinician then preferably observes a blood flashback along catheter adapter 24 and/or integrated extension tube 25.

Figure 9A:
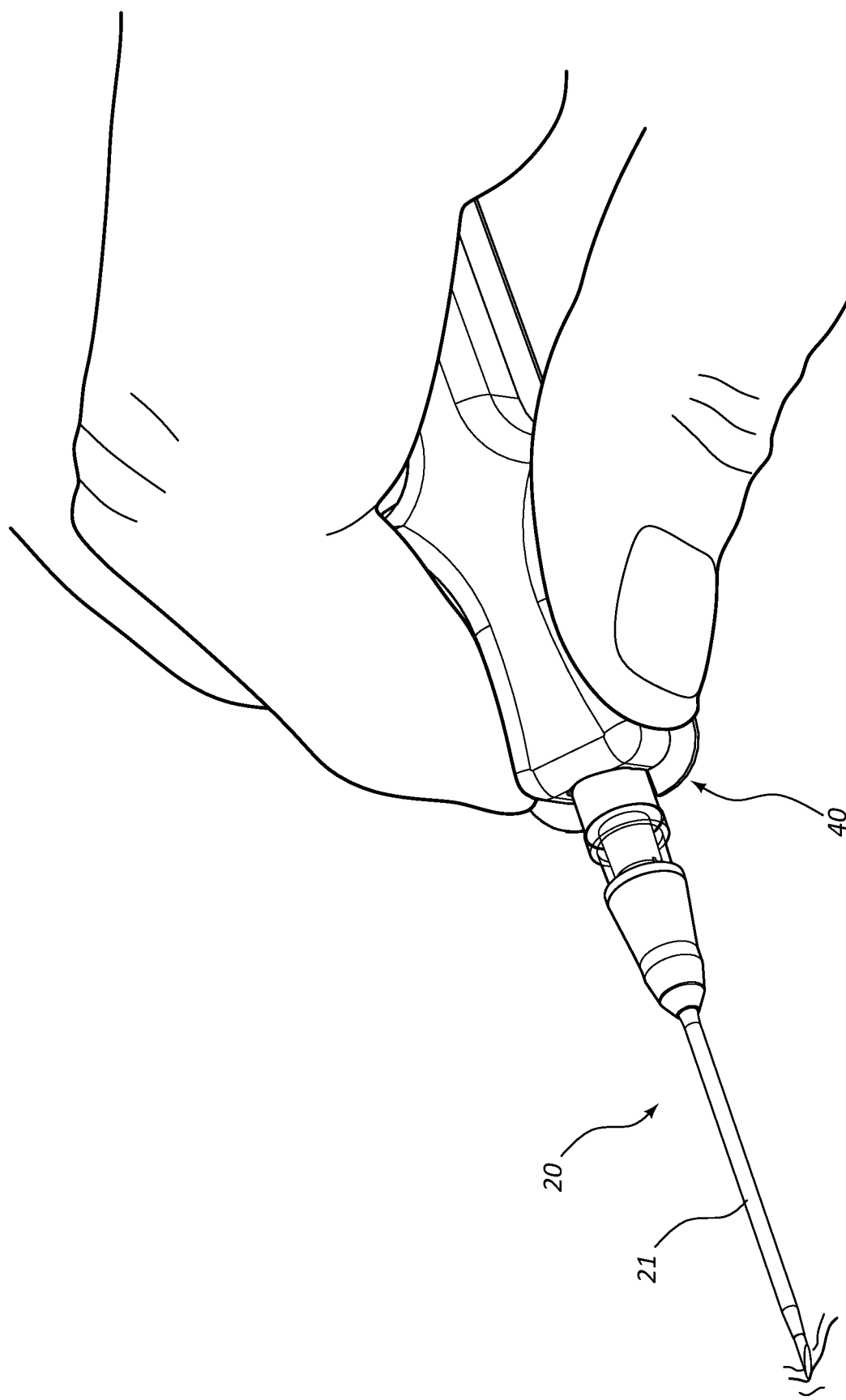
FIG. 9A is a side elevation view of an integrated package and gripping device in accordance with a representative embodiment of the present invention ready for use and the clinician's fingers in the position used for inserting the catheter into a patient's vasculature.
Figure 9B:
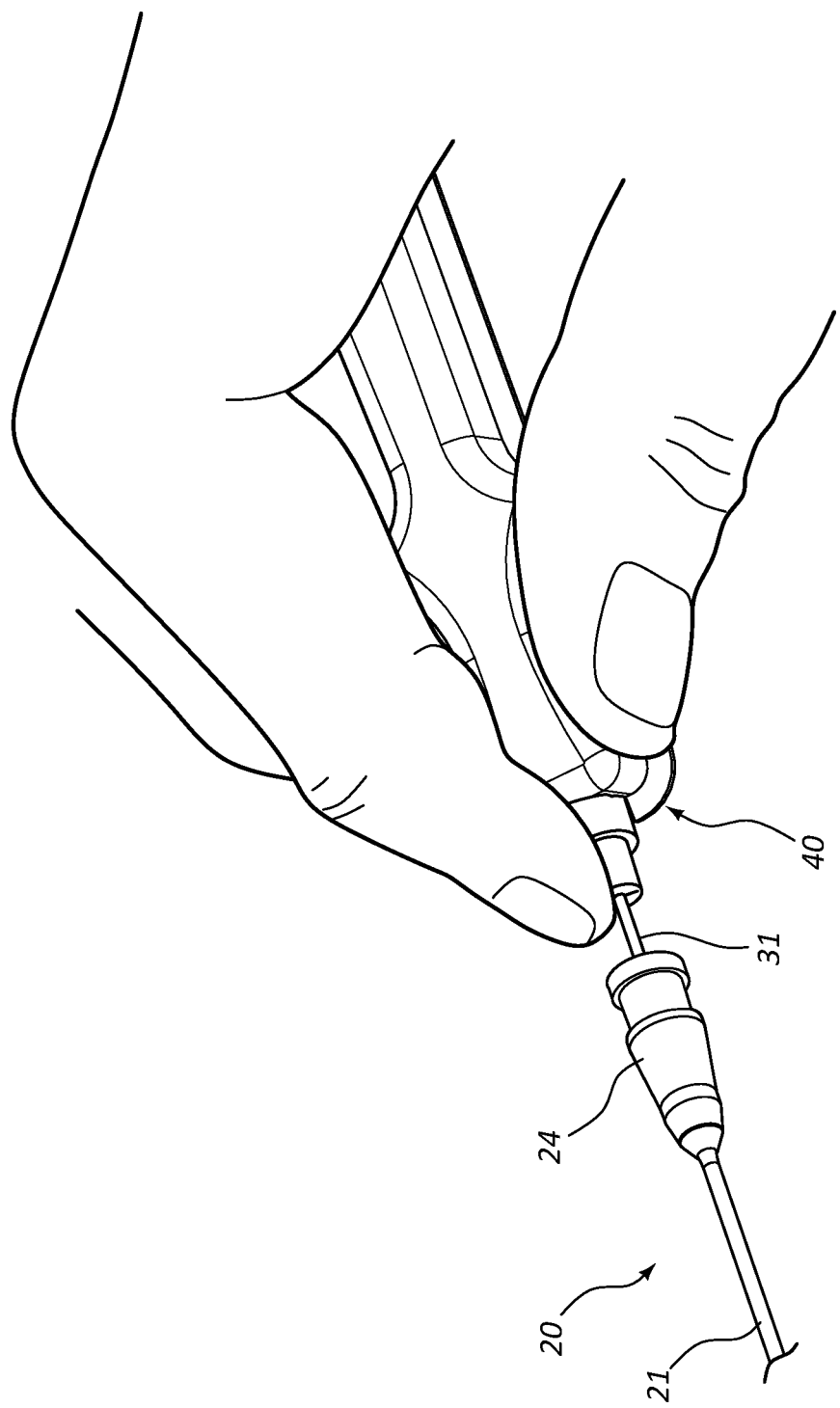
FIG. 9B is a side elevation view of the device of FIG. 9A wherein the catheter has been advanced distally with respect to the introducer needle sub-assembly in accordance with a representative embodiment of the present invention.
Figure 9C:
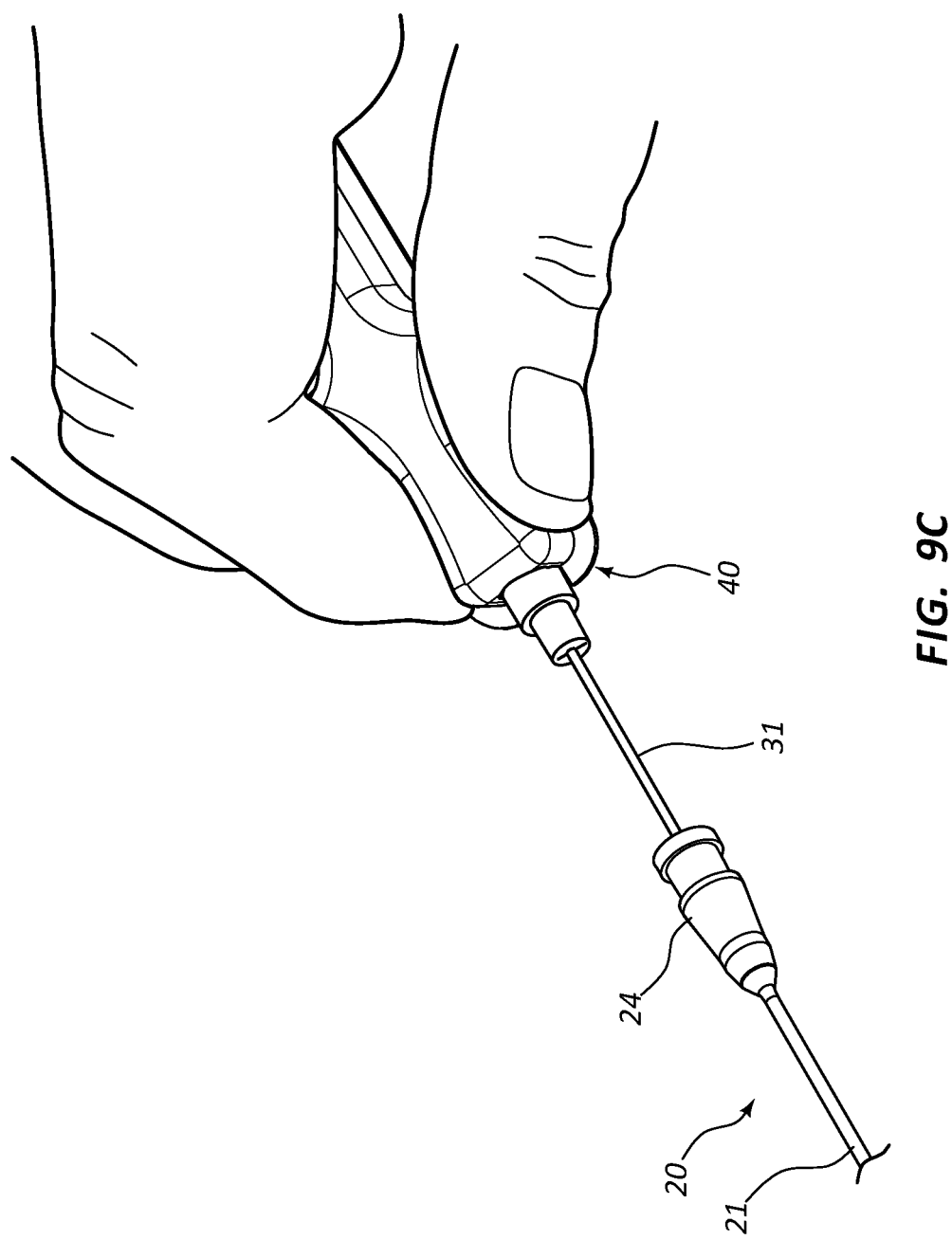
FIG. 9C is a side elevation view of the device of FIG. 9B wherein the catheter has been advanced further distally.
Figure 9D:
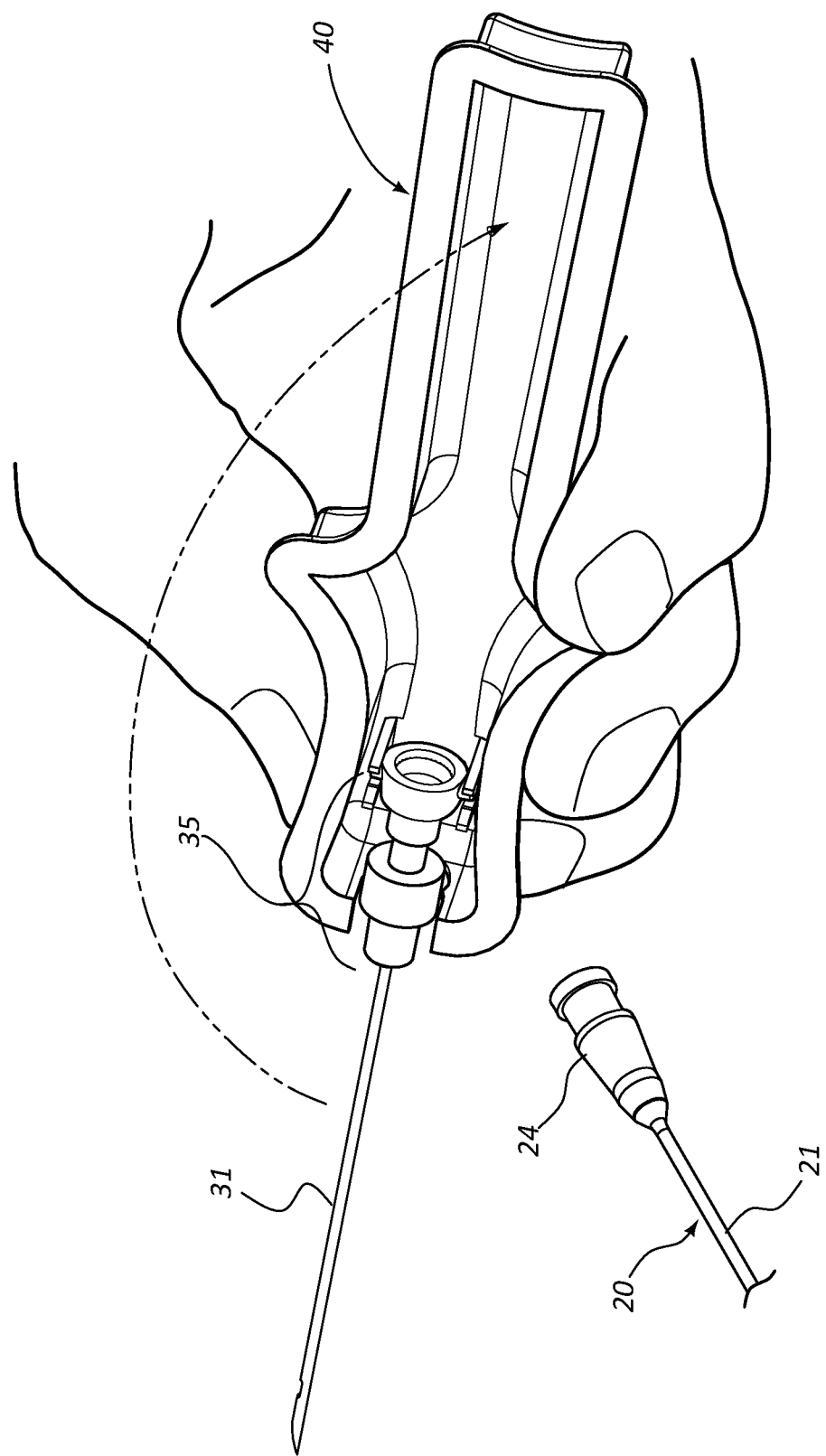
FIG. 9D is a bottom elevation view of the device of FIG. 9C wherein the catheter has been fully advanced with respect to the introducer needle sub-assembly in accordance with a representative embodiment of the present invention.
Figure 9E:
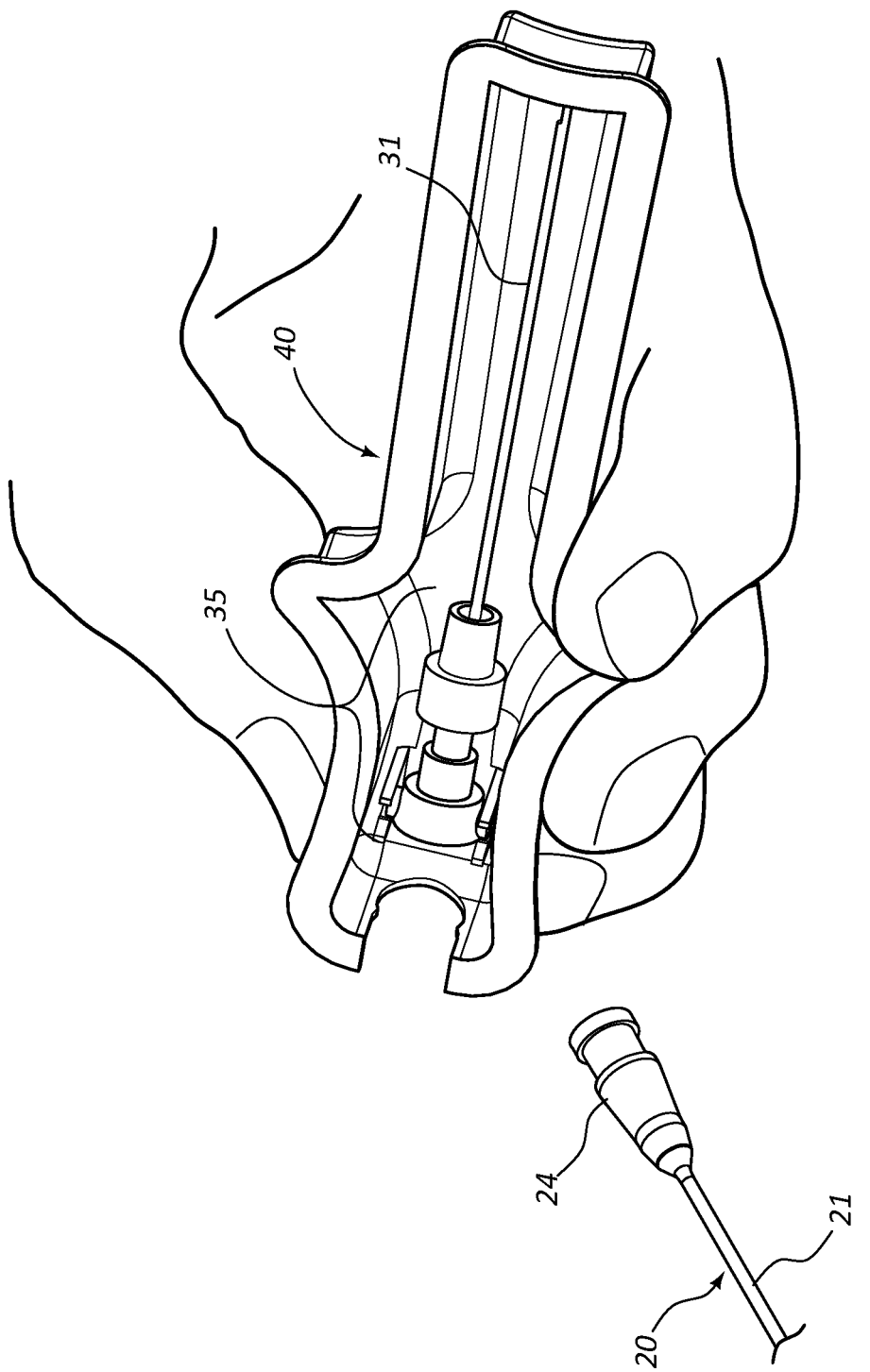
FIG. 9E is a bottom elevation view of the device of FIG. 9D wherein the introducer needle sub-assembly has been deactivated or returned to the closed position in accordance with a representative embodiment of the present invention.

As generally depicted in FIGS. 9A through 9E, after confirming placement of introducer needle 31 and catheter 21 in the target blood vessel, the clinician advances catheter 21 distally axially along introducer needle 31 into position in the blood vessel by pushing against catheter adapter 24 (see FIG. 9B). In certain techniques, introducer needle 31 may be partially withdrawn proximally into catheter 21 before catheter 21 is completely advanced into position in the blood vessel. After proper placement of catheter 21 is achieved, the clinician places a finger (from her other hand) on the patient's skin over the blood vessel approximately over distal end 23 of catheter 21. By placing a finger on the patient's skin and applying sufficient pressure on the skin, the clinician thereby substantially occludes or at least minimizes blood flow through catheter 21. The clinician then places one finger against catheter adapter 24 and simultaneously pulls on needle hub 35 via package grip assembly 40 in order to move needle hub 35 proximally and thus withdraw introducer needle 31 from catheter 21 (see FIGS. 9B-9D).

In embodiments comprising a needle shield or shroud, as needle hub 35 is moved proximally with respect to catheter 21, the sharp distal tip 32 enters into and is trapped in the needle shield. Regardless of whether a needle shroud is employed, introducer needle assembly 30 is then transitioned into a closed or deactivated position within package grip assembly 40 (see FIG. 9E). Introducer needle assembly 30 and package grip assembly 40 (which doubles as a sharps protection shield following use of device 10) may then be disposed of according to the facility's disposal protocol. Thus, it is seen that an introducer needle assembly and corresponding package grip assembly is provided that allows a catheter to be inserted by a clinician using virtually any clinically acceptable technique and regardless of whether a ported catheter or a straight catheter is being inserted into a patient.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A medical device, comprising:
 an introducer needle assembly, comprising:
  an introducer needle comprising a proximal end and a distal tip; and
  a needle hub coupled to the proximal end of the introducer needle;
 a package comprising an internal cavity; and
 a hinge assembly disposed within the internal cavity of the package, wherein the introducer needle assembly is hingedly coupled to the package at the hinge assembly, wherein the hinge assembly facilitates rotation of the distal tip of the introducer needle from a shielded position within the internal cavity of the package to an insertion position outside the package.

2. The device of claim 1, further comprising wing formations, wherein the package further comprises external lateral sides, wherein the wing formations are attached to at least a portion of the lateral sides of the package, wherein the wing formations each have a proximal edge and a distal edge.

3. The device of claim 2, wherein the proximal and distal edges of the wing formations are concave.

4. The device of claim 3, further comprising a sealing label removably attached to the package, wherein the removable sealing label sterilely seals the internal cavity.

5. The device of claim 4, wherein the sealing label is removably attached to the needle hub, and wherein removal of the sealing label activates the device by pulling the introducer needle and catheter from the shielded position within the internal cavity to the insertion position.

6. The device of claim 5, wherein the hinge assembly further comprises a biasing mechanism, wherein the integral biasing mechanism restrains the device in one of the shield position or the insertion position.

7. The device of claim 6, wherein the biasing mechanism is comprised of one or more protuberances formed on one of the package and the needle hub and one or more corresponding cavities formed on the other of one of the package and the needle hub.

8. The device of claim 7, further comprising a flange attached to an external perimeter of the package.

9. The device of claim 8, wherein the needle hub is hingedly coupled to the package by the hinge coupling assembly.

10. The device of claim 9, wherein the biasing mechanism is comprised of one or more elliptical axel bosses.

11. An apparatus for housing and gripping a catheter, the apparatus comprising:
 a body having lateral sides and defining a cavity having a proximal end and a distal end;
 a sealing label configured to cover the cavity and removably coupled to the body;
 wing formations disposed on the lateral sides of the body, wherein the wing formations are adapted to enhance the gripping surface of the body;
 an introducer needle assembly, comprising:
  an introducer needle comprising a proximal end and a distal tip; and
  a needle hub coupled to the proximal end of the introducer needle;
 and
 a catheter coaxially and slidably disposed about the introducer needle, wherein the introducer needle and the catheter are contained within the cavity defined by the body prior to use, wherein the introducer needle assembly is coupled to the body within the cavity, wherein the coupling is located within the distal end of the cavity.

12. The apparatus of claim 11, wherein the sealing label sterilely seals the cavity defined by the body prior to use.

13. The apparatus of claim 12, further comprising a flange formed about an external perimeter of the body.

* * * * *